United States Patent [19]
Shimizu

[11] Patent Number: 4,818,492
[45] Date of Patent: Apr. 4, 1989

[54] CAPACITIVE LIQUID LEVEL SENSOR FOR AUTOMATIC CHEMICAL ANALYZER

[75] Inventor: Yoshiaki Shimizu, Nishinasuno, Japan

[73] Assignee: Kabushiki Kaisha Toshiba, Kawasaki, Japan

[21] Appl. No.: 28,705

[22] Filed: Mar. 20, 1987

[30] Foreign Application Priority Data

Mar. 20, 1986 [JP] Japan ................. 61-63075

[51] Int. Cl.$^4$ ............................................. B01L 3/02
[52] U.S. Cl. ................. 422/100; 73/863.02; 73/864.24; 422/63
[58] Field of Search ........... 73/863.01, 863.02, 864.24; 422/100, 67, 63; 436/49, 180; 324/61 R

[56] References Cited

U.S. PATENT DOCUMENTS

| | | |
|---|---|---|
| 3,391,547 | 7/1968 | Kingston . |
| 3,635,094 | 1/1972 | Oberli ............................ 73/864.24 X |
| 3,754,444 | 8/1973 | Ure et al. .......................... 73/863.01 |
| 4,228,831 | 10/1980 | Kerns ................................ 422/100 X |
| 4,325,909 | 4/1982 | Coulter et al. ................... 422/100 X |
| 4,451,433 | 5/1984 | Yamashita et al. ..................... 422/63 |
| 4,487,836 | 12/1984 | Takayanagi et al. ........ 73/863.01 X |

Primary Examiner—Michael S. Marcus
Attorney, Agent, or Firm—Oblon, Fisher, Spivak, McClelland & Maier

[57] ABSTRACT

A capacitive liquid level sensor for an automatic chemical analyzer, wherein a pipetting tube approaches a liquid level of the sample to be analyzed and is electrically connected to one terminal of an electrical bridge network. The electrical bridge network is activated by an A.C. current and produces an A.C. signal which has a phase change produced by a change in capacitance between the pipetting tube and the liquid level as the pipetting tube approaches the liquid level. The A.C. signal is converted into a D.C. signal proportional to the phase difference by means of a phase detector. A liquid level is detected by comparison of the D.C. signal with a preselected reference level.

5 Claims, 4 Drawing Sheets

CAPACITIVE LIQUID LEVEL SENSOR FOR AUTOMATIC CHEMICAL ANALYZER

BACKGROUND OF THE INVENTION

1. Field of the Invention

The present invention relates to a liquid level sensor for an automatic chemical analyzer, and more particularly to a capacitive liquid level sensor which is used not only as a liquid level sensor, but also as a pipetting tube in the automatic chemical analyzer.

2. Discussion of the Background

An automatic chemical analyzer automatically analyzes a plurality of samples such as patient serums according to a number of analysis items. The samples in a sample container are dispensed to an array of reaction vessels using a pipetting tube. Reagent solutions selected in accordance with the analysis items are fed to the reaction vessels using another pipetting tube. The reaction solutions in the reaction vessels are analyzed, for example, by ion selecting electrodes for measuring ion activities like sodium, potassium and chlorine or by a spectrometer for spectral analysis. The results of such analyses are displayed on a monitor or typed, analysis item by item, and, patient by patient.

In the conventional automatic chemical analyzer, a liquid level sensor cooperates with such a pipetting tube for detecting the liquid level of the samples in the sample container or reagent solutions of the reagent solution tanks. A deep immersion of the pipetting tube results in excess liquid sticking to outside of the pipetting tube. This excess liquid, not only decreases accuracy of the pipetting, but also, causes contamination with another sample or reagent solution. The inaccuracy of the pipetting and contamination caused by the excess liquid sticking to the outside of the pipetting tube makes the analysis results inaccurate and less reliable.

In other words, shallow immersion of the pipetting tube gives accurate and reliable analysis results. A liquid level sensor enables such a shallow immersion of the pipetting tube and avoids deep and blind immersion of it.

A conventional liquid level sensor is described in for example, U.S. Pat. No. 4,451,433. The conventional liquid level sensor comprises a pair of electrically conductive members. One is a pipetting tube made of a chemical proof metal such as platinum or stainless steel and the other is an electrode made of a chemical proof metal wire. Such a pair of electrically conductive members provides a detection signal when both are immersed into a reagent solution or samples.

However such a conventional liquid level sensor may cause inaccurate and contaminated pipetting because the electrode accompanying the pipetting tube is immersed as well as the pipetting tube. Liquid sticking to the electrode is liable to produce less accurate and more contaminated pipetting.

Further, it is difficult in the conventional liquid level sensor to watch and evaluate whether or not the suction of the pipetting tube is normal.

SUMMARY OF THE INVENTION

It is, therefore, a primary object of the present invention to provide a capacitive liquid level sensor for an automatic chemical analyzer which is able to detect a liquid level only with a pipetting tube.

It is another object of the present invention to provide a capacitive liquid level sensor which enables a visual determination as to whether or not the suction of the pipetting tube is normal.

These and other objects are achieved according to the present invention by providing a new and improved liquid level sensor including an electrical bridge network, a pipetting tube connecting to an element of the electrical bridge network which when it approaches the liquid level changes a capacitance between the liquid level and the pipetting tube, a source of A.C. current connected to a terminal of the bridge network such that changes in the capacitance between the liquid level and the pipetting tube produce an A.C. output signal from the bridge network, a phase shift detector for comparing the phase of the bridge output A.C. signal with the phase of the A.C. current applied to the bridge network to produce a D.C. output signal dependent on the distance between the liquid level and the pipetting tube, and a comparator for comparing the D.C. output signal with a preselected reference level to determine whether or not the pipetting tube has reached the liquid level.

It is another feature of the present invention that the liquid level sensor further detects the amplitude of the D.C. output signal to determine whether or not the suction by the pipetting tube is normal.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENT

Figure 1:
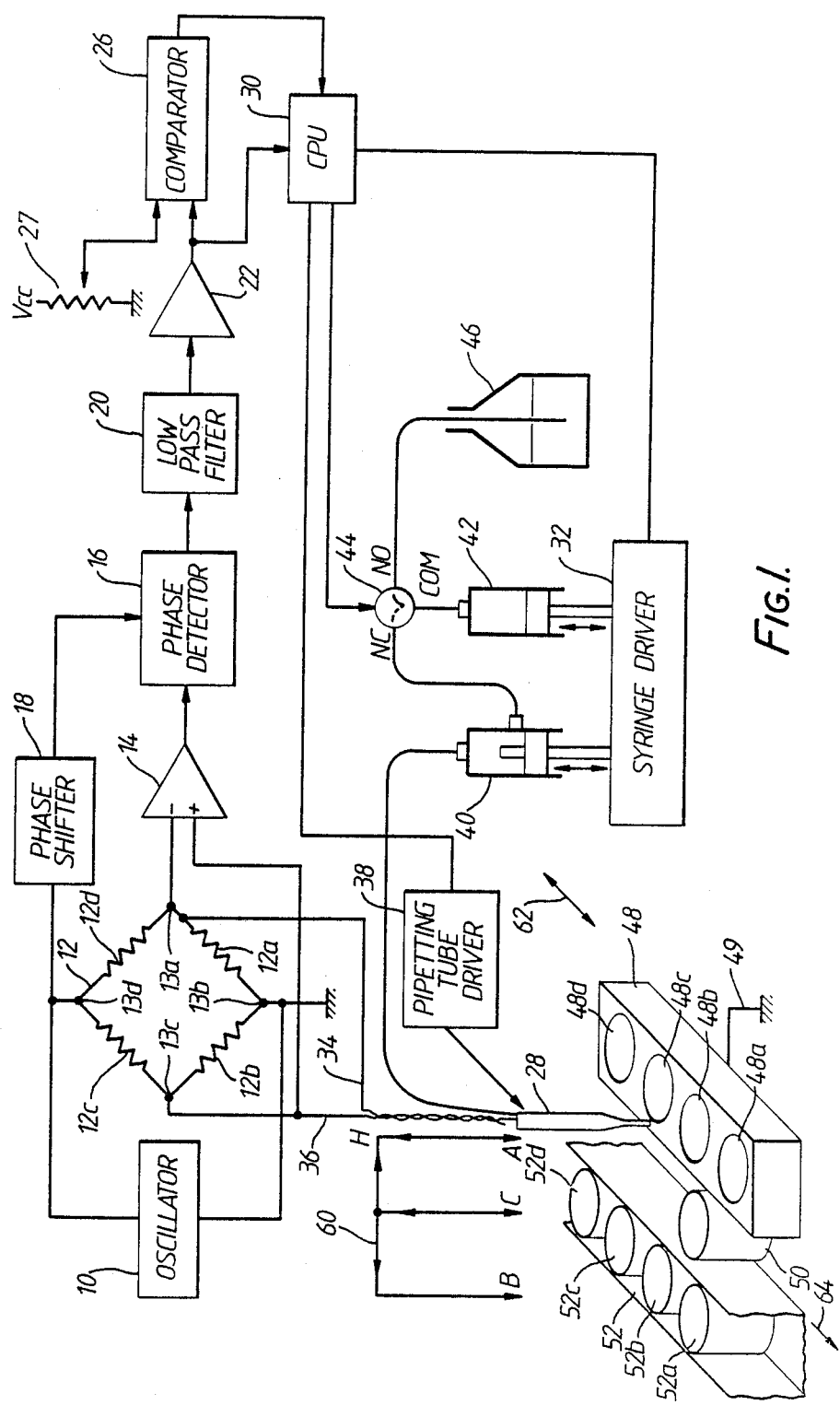
FIG. 1 is a block diagram illustrating an embodiment of a capacitive liquid sensor for an automatic chemical analyzer in accordance with the present invention.

Referring now to the drawings, wherein like reference numerals designate identical or corresponding parts throughout the several view, FIG. 1 illustrates a block diagram of an embodiment of a capacitive liquid level sensor for an automatic chemical analyzer in accordance with the present invention. A pipetting tube 28 is made of a chemical proof metal such as platinum or stainless steel and is driven by a pipetting tube driver 38. The pipetting tube driver 38 includes a drive mechanism (not shown), such as stepping motors and a rack and pinion mechanism, which causes the pipetting tube 28 to move horizontally and vertically from a home position H to a suction position A, from the suction position A to a discharge position B, from the discharge position B to a cleaning position C and from the cleaning position C to the home position H, as shown by the arrows 60. At the suction position A a sample container array 48 is disposed. The sample container array 48 includes sample cups 48a–48d loaded with samples, such as patient serums and is movable in direction 62 to arrange each sample cup 48a–48d at the suction position A. As shown, the sample container array 48 includes four cups 48a–48d, but in practice the number of cups may be more or less than four.

Also shown in FIG. 1 is a reaction vessel array 52 which circulates through the discharge position B. The reaction vessel array 52 includes a number of reaction vessels 52a–52d, the number of which likewise is not limited to four. At the cleaning position C, a cleaning section 50 is disposed to clean both the inside and outside of the pipetting tube 28.

The pipetting tube 28 is linked to a microsyringe 40 through a flexible tube to pass a liquid or air. The microsyringe 40 sucks, holds, and discharges exact amounts of the sample. The microsyringe 40 is linked to a syringe 42 via valve 44. The syringe 42 sucks and discharges a sufficient amount of a cleaning liquid, such as deionized water, contained in a cleaning liquid bath 46 to clean the inside of the pipetting tube 28. The microsyringe 40 and syringe 42 are driven by a syringe driver 32. The valve 44 is common (COM) to the syringe 42, normally open (NO) to the liquid bath 46 and normally close (NC) to the microsyringe 40. In other words, when a control signal is supplied from a CPU 30 to the valve 44, the valve 44 links the syringe 42 to the microsyringe 40. Otherwise, it links the syringe 42 to the liquid bath 46.

The pipetting tube is electrically connected to a terminal 13a of a bridge network 12 by a sensing cable 34. Since the pipetting tube 28 is made of a conductive material, the tip of the pipetting tube 28 is electrically connected to the terminal 13a of the bridge 12. From another terminal 13c of the bridge 12 diagonal to the terminal 13a where the sensing cable is connected, a compensating cable 36 extends near the pipetting tube 28, but is electrically insulated from both the pipetting tube 28 and the sending cable 34. In the preferred embodiment, the sending cable 34 and the compensating cable 36 are twisted together.

The bridge 12 includes four impedance elements 12a–12d such as resistors and four terminals 13a–13d. An oscillator 10 is connected to the diagonal terminals 13b, 13d of the bridge 12 and also to a phase shifter 16. The ocsillator supplies an A.C. current to the terminals 13b, 13d of the bridge 12 and the phase shifter 16. In the preferred embodiment, the frequency of the A.C. current is more than 10 KHz.

The stray capacitance Cx between the pipetting tube 28 and the liquid level, more precisely the ground of the sample container 48, is less than 1 pF. The impedance of the stray capacitance Cx caused by the A.C. current applied from the ocillator 10 is represented as $1/jw\,Cx$, and rewritten as $Z(w)e^{j\phi(w)}$, where $Z(w) = \frac{1}{wCx}$ $\phi(w) = \tan^{-1}(-1/wCx)$, and w is a frequency of the A.C. circuit.

In the case that Cx is 0.1 pF and w is 100 KHz, the impedance of the capacitance becomes about 10 MΩ.

Accordingly, the resistors 12a–12d are preferrably set to about 10 MΩ.

Figure 3A:
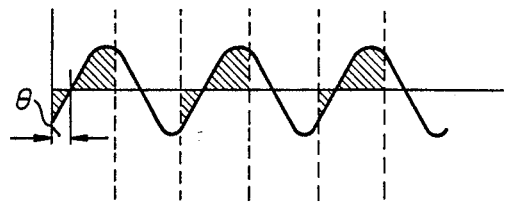
FIGS. 3A, 3B and 3C are timing diagrams illustrating wave shapes to explain the phase detection performed by the phase detector shown in FIG. 1.
Figure 3B:

The diagonal terminals 13a, 13c are connected to a differential amplifier 14 which amplifies the output of the terminals 13a, 13d. The phase shifter 18 varies the phase of the A.C. current and supplies the phase-varied A.C. current to a phase detector 16. The phase detector 16 converts the phase-varied A.C. current into a square wave and phase-detects the output, as shown in FIG. 3A, of the amplifier 14 with the square wave as shown in FIG. 3B. A low pass filter 20 converts the output of the phase detector into a D.C. signal and supplies the same to an amplifier 22. A reference level generator 24 generates a preselected reference level corresponding to the level when the pipetting tube 28 reaches the liquid level of the sample in the sample cup 48b. A comparator 26 compares the D.C. signal from the amplifier 22 with the preselected reference level and provides a detection signal to a CPU 30 when the D.C. signal exceeds the preselected reference level. The CPU 30 controls the pipetting tube driver 38 in accordance with the detection signal provided from the comparator 26. The CPU 30 further controls the sequences of the pipetting tube driver 38, the syringe driver 32, the valve 44 and the movements of the sample container array 48 and the reaction vessel array 52 and other units (not shown). After the pipetting tube finishes its suction and leaves the liquid level, the CPU 30 checks the amplitude of the D.C. signal provided from the amplifier 22 to determine whether or not the suction is normal.

Now the operation of the above-described embodiment will be explained. First, the pipetting tube 28 is lowered from its home position H to the suction position A. During lowering the stray capacitance between the tip of the pipetting tube 28 and the liquid level of the sample cup 48b increases gradually. The disturbance capacitance Ce between the bridge 12 and the pipetting tube 28 also varies and is detected by the cable 34 because the distance between them changes. But this disturbance capacitance Ce is cancelled by the compensating cable 36.

Figure 2:
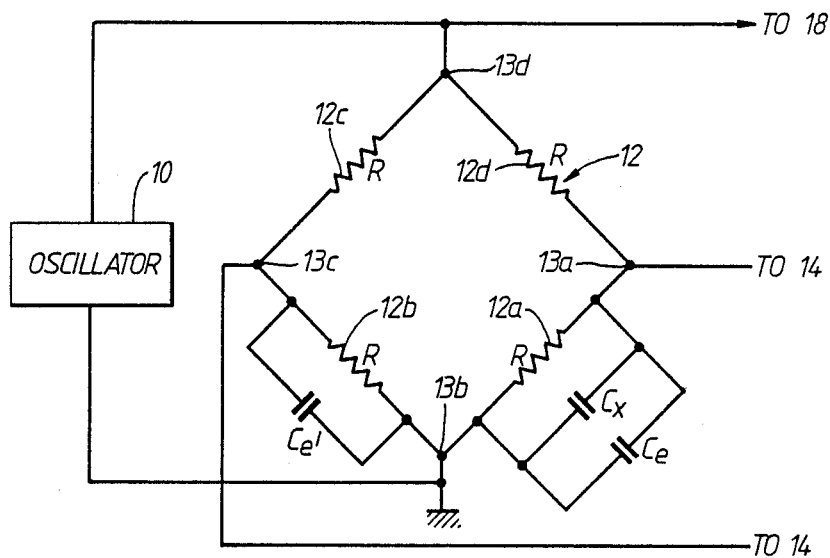
FIG. 2 is an equivalent circuit for the bridge shown in FIG. 1.

Referring to FIG. 2, which illustrates the equivalent circuit of the bridge 12, the terminals 13a and 13b contain the stray capacitance Cx and disturbance capacitance Ce therebetween. However, the capacitance C'e nearly equal to the capacitance Ce is detected by the compensating cable 36. Both the capacitances C'e and Ce are the same polarity to the input terminals of the differential amplifier 14. Accordingly, the disturbance capacitance is cancelled by the compensating cable 36.

The output of the bridge 12 depends on only the stray capacitance Cx. Its phase θ varies in accordance with the stray capacitance.

Figure 3C:
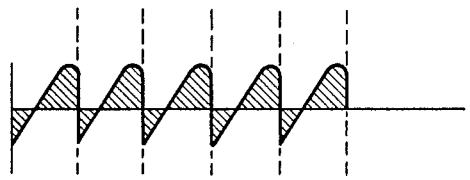

The phase detector 16 receives the output, as shown in FIG. 3A, of the bridge 12 through the amplifier 14 and phase-detects the same in relation to the square wave as shown in FIG. 3B to produce the phase-detected signal as shown in FIG. 3C. The phase-detected signal is supplied to the low pass filter 20 to produce the D.C. signal. If there is 90 degree phase difference between the output signal as shown in FIG. 3A and the square wave FIG. 3B, the D.C. signal becomes zero. This is explained more precisely as follow.

The Fourier series el(t) of the square wave is described as $$e1(t) = \frac{4A}{\pi}\left(\sin(wt) + \frac{1}{3}\sin(3\ wt) + \frac{1}{5}\sin(5\ wt) + \ldots\right)$$

where A is the amplitude of the square wave. Then the output signal e2(t) is written as $$e2(t) = S(t)\sin(wt-\theta)$$

where S(t) is the amplitude of the output signal and $\theta$ represents the phase difference between the output signal and the A.C. current. The phase-detected signal e3(t) is represented as $$\begin{aligned} e3(t) &= e1(t) \cdot e2(t) \\ &= \frac{4AS(t)}{\pi}\sin(wt - \theta)\cdot\left(\sin(wt) + \frac{1}{3}\sin(3\ wt) + \ldots\right) \end{aligned}$$

After filtering by the lowpass filter 20, e3(t) is approximately as follow:

$$\begin{aligned} e3(t) &= \frac{4AS(t)}{\pi}\sin(wt - \theta)\sin(wt) \\ &= \frac{2}{\pi}AS(t)\cos\theta \end{aligned}$$

This means that the D.C. signal is proportional to the amplitude S(t) and cos $\theta$ which depends on the stray capacitance Cx.

In the preferred embodiment, the phase of the square wave as shown in FIG. 3B is adjusted or calibrated by the phase shifter 18 so that the D.C. signal becomes zero when the pipetting tube 28 is located at the home position H. This D.C. signal increases as the pipetting tube 28 approaches the liquid level of the sample as shown in FIG. 4.

Figure 4:
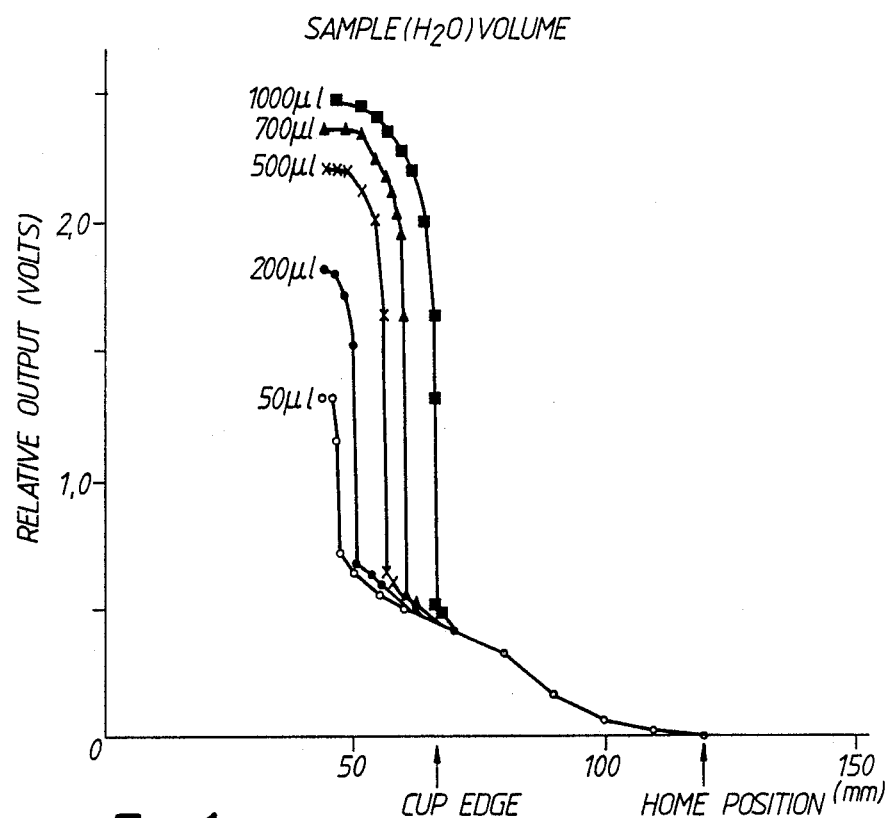
FIG. 4 is a graph showing experimental results of a D.C. signal produced by the amplifier 22 as shown in FIG. 1 regarding various quantities of sample.

FIG. 4 illustrates the respective D.C. signals wherein the sample quantity in the sample cup of the volume 1000$\mu$ varies from 50 $\mu$l to 1000 $\mu$l. These experimental results indicate that the D.C. signals change significantly when the pipetting tube is near the liquid level. If the preselected reference level generated by the generator 24 is set to approximately 1 volt, the liquid level will be completely detected with respect to a volume of liquid from 50 $\mu$l to 1000 $\mu$l.

Figure 5:
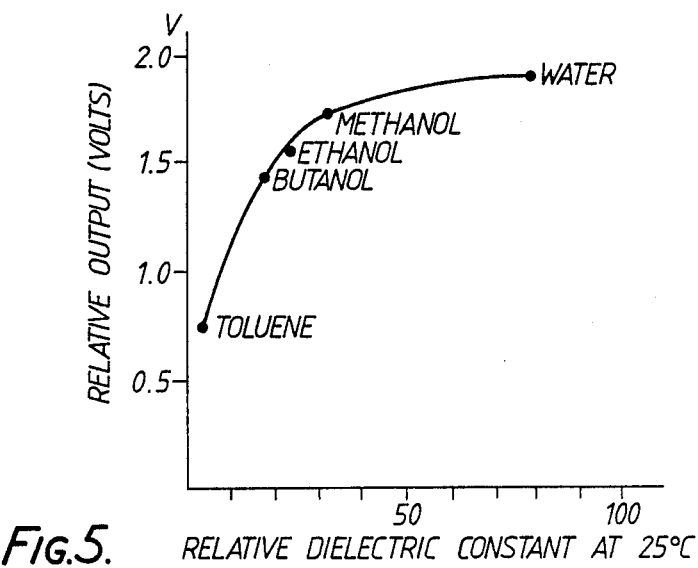
FIG. 5 is a graph showing experimental results of the D.C. signal in relation to materials having different dielectric constants.
Figure 6:
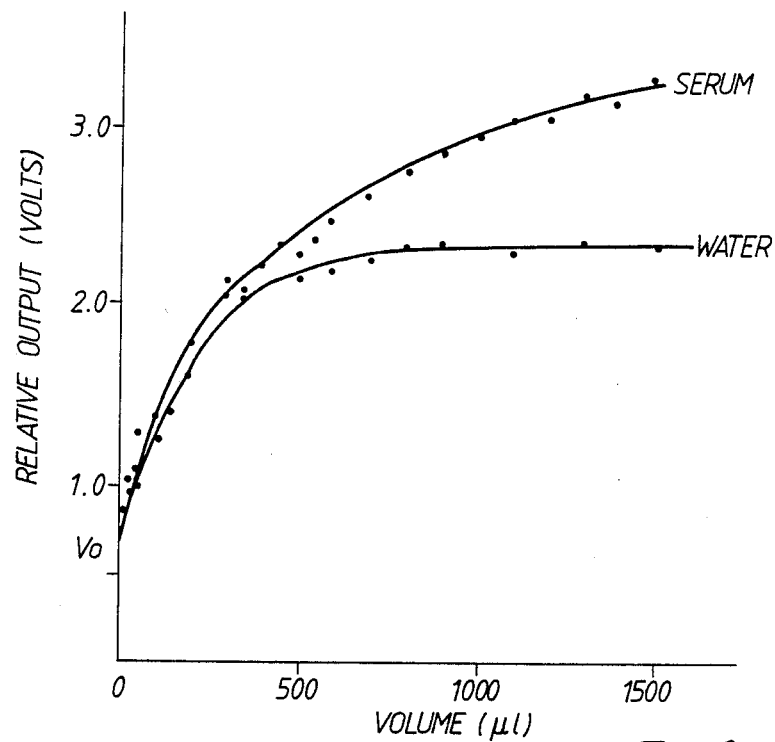
FIG. 6 is a graph showing experimental results of the D.C. signal in relation to differing suction volumes of a water and serum.

Since the capacitance Cx is proportional to the dielectric constant of the material, the D.C. signal provided from the amplifier 22 increases or decreases according to the dielectric constant between the pipetting tube 22 and the ground 49. FIG. 5 indicates the D.C. signals regarding toluene ($C_6H_5CH_3$), butanol ($C_4H_9OH$), ethanol ($C_2H_5OH$), methanol ($CH_3OH$), and water ($H_2O$) of the same volume. Thus, the D.C. signals depend on the dielectric constant of the material. FIG. 6 shows curves of the D.C. signals of water and serum, obtained by varying the volumes thereof. The dielectric constant of the serum is higher than that of water. Furthermore the larger the volume of the sample is, the higher the D.C. signal is, as shown in FIG. 6. Therefore the preselected reference level is determined according to the material and its range of volume.

When the CPU 30 receives the detection signal from the comparator 26, the CPU 30 controls the pipetting tube driver 38 so that the pipetting tube 28 is immersed as shallow as possible, but deep enough not so as to suck air. Then, the microsyringe 40 is activated by the CPU 30 such that the pipetting tube 28 sucks a certain amount of the sample. In the preferred embodiment, the microsyringe 40 and the tube between the pipetting tube 28 and the microsyringe are filled with the cleaning liquid. There is an air bubble to isolate the sucked sample and the cleaning liquid in the pipetting tube.

Next, the pipetting tube 28 holding the samples moves from the suction position A to the discharge position B. In the case of plurality of analysis items to be performed on the sample, the pipetting tube 28 at once sucks and holds sufficient sample to discharge into the reaction vessels in amounts equal to the analysis items. The pipetting tube 28 at the discharge position B discharges the held sample into the reaction vessels in amounts equal to the analysis items, synchronized with the step by step movement of the circulating reaction vessel array 52 and activation of the microsyringe 40.

After finishing discharging the sample, the pipetting tube 28 moves from the discharge B to the cleaning position C. The cleaning section 50 at the cleaning position C washes the outside of the pipetting tube with a cleaning liquid such as deionized water, which is also provided via the activation of the syringe 42 to the inside of the pipetting tube 28. Cleaning liquid is discharged from the pipetting tube 28 to clean the inside of it.

Then, the cleaned pipetting tube 28 is returned from the cleaning position C to the suction position A. The sample container array 48 moves one step to arrange the next sample cup at the suction position A. In this way the above operation is repeated.

The reaction vessels loaded with the samples moves to the reagent pipetting section (not shown). In this section, the reagents corresponding to the analysis items are discharged into the respective reaction vessels by a reagent pipetting tube which sucks and discharge such reagents. In the preferred embodiment, the reagent pipetting tube also includes a liquid level sensor the same as that provided for the pipetting tube 28, as shown in FIG. 1. This liquid level sensor contributes not only to accurate discharge of reagent and less contamination with another reagent, but also detection of the rest of the reagent.

After discharge of the reagent, the reaction vessels loaded with the reagent solution are transferred through a reaction section (not shown) which includes a temperature-maintained bath kept over the range between 25° C. and 37° C. Then the reagent solutions are analyzed by analyzers, such as ion selective electrodes, a spectrometer and a photometer. The CPU 30 acquires such data analyzed by the analyzers and outputs the analyzed data to the monitor or printer, sample by sample and item by item.

In the preferred embodiment, the pipetting tube 28 sucks much sample little by little, synchronized with the gradual immersion of the pipetting tube 28. After detection of the liquid level, the pipetting tube 28 is immersed deep enough to suck a portion of the sample, but not so deep as it sucks the entire amount of the sample. After suction of the portion of the sample, the pipetting tube 28 is further lowered to repeat the suction until it finishes suction of the entire amount of the sample. Suction of portions of the sample is facilitated by the microsyringe 40 driven by the syringe driver 32 under control of the CPU 30 responsive to the detection signal provided from the comparator 26.

Next, the monitoring operation of this embodiment according to the present invention will be explained. After finishing sucking the sample, the pipetting tube 28 leaves the liquid level holding the sample, and moves from the suction position A to the discharge position B via the home position H. When the pipetting tube 28 is located sufficiently far away from the liquid level, like at the home position H, the D.C. signal becomes independent of the liquid level. Furthermore, since the phase detector 16 is calibrated so as to output zero when the pipetting tube 28 is located at the home position H and filled with deionized water, the D.C. signal is not zero, if the pipetting tube 28 holds a sample having a dielectric constant which is different from that of water.

Figure 7:
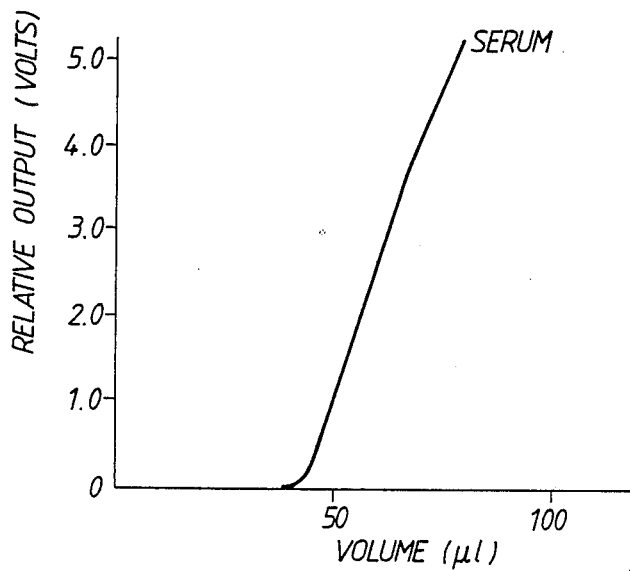
FIG. 7 is a graph of the D.C. signal detected at a home position in relation to various volumes of serum.

FIG. 7 shows a curve of the D.C. signal when the pipetting tube 28 holds different volumes of serums as a sample at the home position H. As shown in FIG. 7, if the pipetting tube 28 holds more than approximately 50 $\mu$l of the serum, the D.C. signal is between zero and one volt. It is verified that the D.C. signal is zero when the pipetting tube 28 sucks air accidentaly, because the dielectric constant of air is less than that of water. This D.C. signal is reliable in this embodiment, because the disturbance capacitance Ce between the pipetting tube 28 and the bridge 12 is cancelled by the compensating cable 36.

The CPU 30 checks the D.C. signal while the pipetting tube 28 is located at home H on the way from the suction position A to the discharge position B after the suction of an amount of serum over 50 $\mu$l. At that time, if the D.C. signal is not detected, the CPU 30 will interrupt the next procedure and cause the pipetting tube 28 to suck the same serum again.

Occasionally the liquid level sensor takes the liquid level from a bubble in the sample and the pipetting tube 28 sucks air. But in this embodiment such an erroneous suction is automatically detected before discharge. A conventional liquid level sensor only detects the liquid level of the sample, but does not detect whether the suction was normal or not.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A capacitive liquid level sensor for an automatic chemical analyzer, comprising:
    pipetting tube means for approaching a liquid level of a sample to suck the sample;
    an electrical bridge network including four impednace elements and four terminals, a first of the four terminals being electrically connected to said pipetting tube means by a sensing cable;
    a compensating cable extending from another terminal of said bridge network to said pipetting tube means along the sensing cable, one end of said compensating cable being eletrically connected to said another terminal and the other end being electrically open-circuited for cancelling capacitance between said pipetting tube means and said network bridge means, detected by said pipetting tube means;
    an A.C. source for supplying an A.C. current to said electrical bridge network to enable detecting a change of capacitance corresponding to a distance between the pipetting tube means and the liquid level;
    phase detector means for producing a D.C. output signal representative of a difference in phase between the A.C. current and an A.C. output signal provided from said electrical bridge network; and
    comparing means for comparing the D.C. output signal provided from said phase detector means with a preselected reference level to determine whether or not said pipetting tube means has reached the liquid level.

2. The capacitive liquid level according to claim 1, wherein said compensating cable is twisted with said sensing cable.

3. The capacitive liquid level according to claim 1, wherein said A.C. source is connected to second and fourth diagonal terminal of said electrical bridge and said compensating cable is connected to a third terminal of said electrical bridge.

4. A capacitive liquid level sensor for an automatic chemical analyzer, comprising:
    a pipetting tube which holds a sample sucked from a sample container after being moved to a predetermined position at a distance from the sample container
    an electrical bridge network including four impedance elements and four terminals, one of the four terminals being electrically connected to said pipetting tube by a sensing cable;
    a compensating cable extending from another terminal of said bridge network to said pipetting tube along the sensing cable, one end of said compensating cable being electrically connected to said another terminal and the other end being electrically open-circuited for cancelling capacitance between said pipetting tube and said network bridge means, detected by said pipetting tube;
    an A.C. source for supplying an A.C. current to said electrical bridge network to enable detecting a capacitance caused by the sucked sample in said pipetting tube;
    phase detector means for producing a D.C. output signal representative of a difference in phase between the A.C. current and an A.C. output signal provided from said electrical bridge network; and
    comparing means for comparing the D.C. output signal provided from said phase detector means with a D.C. level preivously obtained with a known material within said pipetting tube when said pipetting tube is located at said predetermined position.

5. The capacitive liquid level according to claim 4, wherein said comparing means compares the D.C. output signal with the D.C. reference level previously obtained with water in said pipetting tube.

* * * * *